US010088339B2

(12) United States Patent
Imanishi et al.

(10) Patent No.: US 10,088,339 B2
(45) Date of Patent: Oct. 2, 2018

(54) AUTOMATED SYSTEM AND METHOD FOR DETECTING DEFECTIVE EDGES OF PRINTED CIRCUIT BOARDS AND OTHER OBJECTS USING MULTIPLE SENSORS

(71) Applicant: Azbil Corporation, Tokyo (JP)

(72) Inventors: Tasuku Imanishi, Santa Clara, CA (US); Shinrin Takahashi, Tokyo (JP)

(73) Assignee: Azbil Corporation, Tokyo (JP)

( * ) Notice: Subject to any disclaimer, the term of this patent is extended or adjusted under 35 U.S.C. 154(b) by 494 days.

(21) Appl. No.: 14/755,612

(22) Filed: Jun. 30, 2015

(65) Prior Publication Data
US 2016/0238372 A1  Aug. 18, 2016

Related U.S. Application Data
(60) Provisional application No. 62/115,849, filed on Feb. 13, 2015.

(51) Int. Cl.
*G01D 5/34* (2006.01)
*G01B 11/245* (2006.01)
*G01N 21/956* (2006.01)

(52) U.S. Cl.
CPC ............ *G01D 5/34* (2013.01); *G01B 11/245* (2013.01); *G01N 21/956* (2013.01); *G01N 2021/95638* (2013.01)

(58) Field of Classification Search
None
See application file for complete search history.

(56) References Cited

U.S. PATENT DOCUMENTS

| 3,676,008 | A | * | 7/1972 | West | G01N 21/89 250/559.45 |
| 4,641,966 | A | * | 2/1987 | Lemmers | G01N 21/88 250/559.22 |
| 8,169,624 | B2 | | 5/2012 | Torii et al. | |

(Continued)

FOREIGN PATENT DOCUMENTS

| JP | 5119496 B2 | 11/2012 |
| JP | 5408915 B2 | 11/2013 |

OTHER PUBLICATIONS

Azbil Corporation, High-Accuracy Position Sensors, K1G Series, CP-PC-2265E, Manual.

(Continued)

*Primary Examiner* — Matthew Reames
*Assistant Examiner* — Steven B Gauthier
(74) *Attorney, Agent, or Firm* — Amster, Rothstein & Ebenstein LLP

(57) ABSTRACT

An automated system and method for detecting substantial edge defects on an object that can degrade or impede proper object performance. The defects, such as chips, cracks, or bumps, if sufficiently substantial, can interfere with the proper operation of the object. The inspection may be performed with four electronic sensors, two on each side of the object, or with two electronic sensors that each take two sets of measurements spaced apart by a certain time interval. Sensor measurements are periodically obtained and used by a controller to calculate a value based on the four sensor measurements. The calculated value is compared to a threshold to determine whether or not any defects are significant.

14 Claims, 14 Drawing Sheets

(56) References Cited

U.S. PATENT DOCUMENTS 8,826,739 B2 9/2014 Matsumoto et al.
2009/0244549 A1 10/2009 Sakaguchi

OTHER PUBLICATIONS

Edge Measurement Sensors (Parallel Laser Light Type) PBZ Series, Brochure.
Keyence America, "GT2 Series—High-Accuracy Digital Contact Sensor", [online] <http://www.keyence.com/products/measure/contact-distance-lvdt/gt2/index.jsp>, retrieved Jun. 18, 2015, 3 pages.
Takenaka Electronic Industrial Co., Ltd., "US-U30AN—Edge Detection Ultrasonic Sensor", [online] <http://www.takex-elec.co.jp/en/product/category/67/series/355>, retrieved Jun. 18, 2015, 1 page.
Keyence America, "IG series—Multi-Purpose CCD Laser Micrometer", [online] <http://www.keyence.com/products/sensor/positioning/ig/index.jsp>, retrieved Jun. 29, 2015, 3 pages.
Omron Corporation, "Omron ZX-GT (laser CCD length measurement sensor)" [online] <http://www.fa.omron.co.jp/products/family/1918/x, retrieved Jun. 29. 2015, 6 pages.

\* cited by examiner

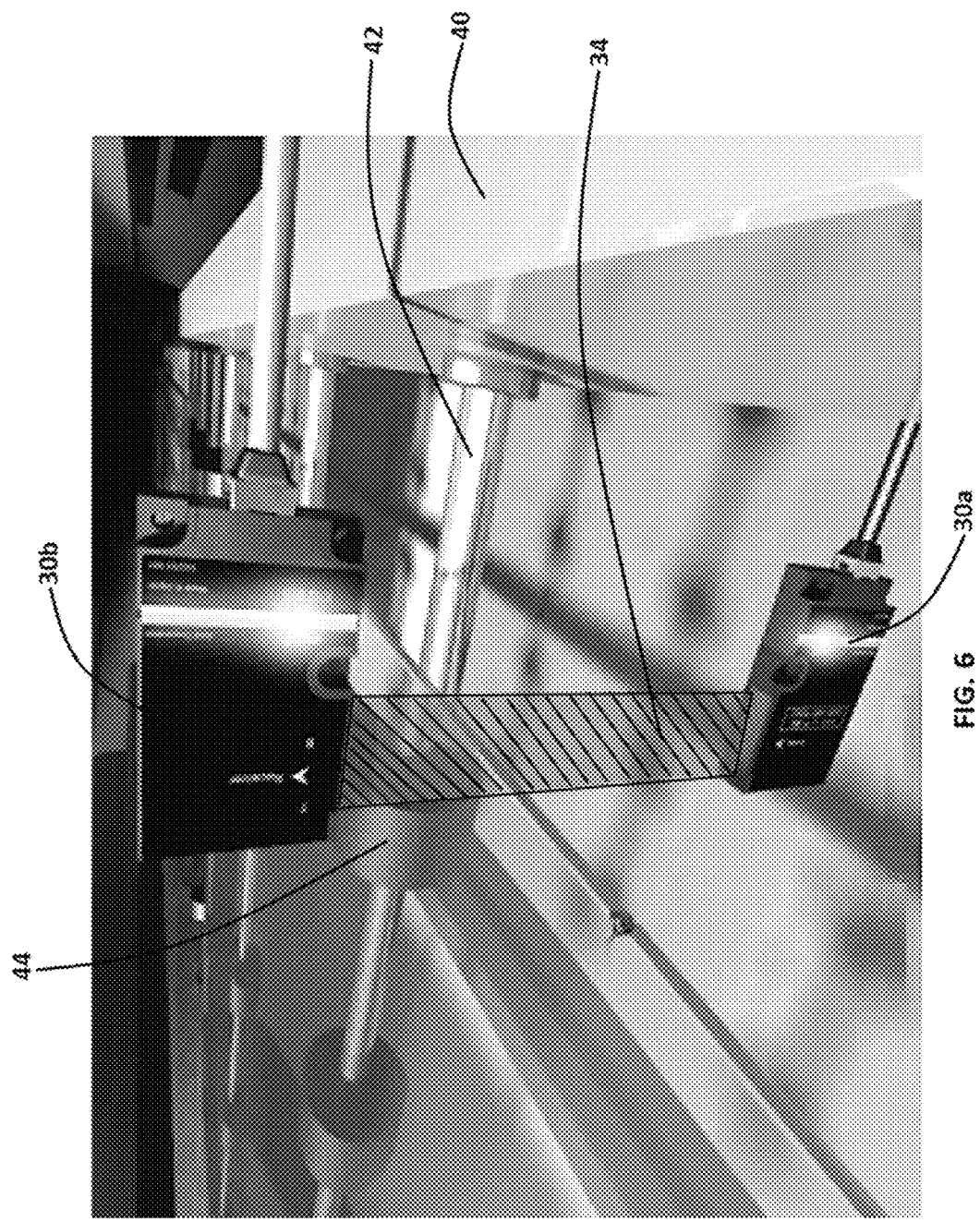

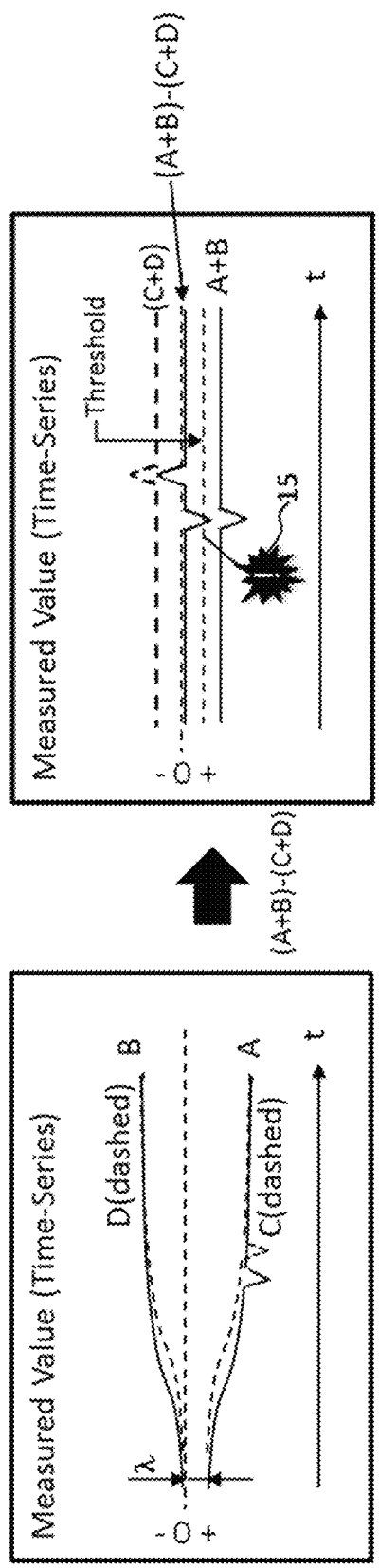

AUTOMATED SYSTEM AND METHOD FOR DETECTING DEFECTIVE EDGES OF PRINTED CIRCUIT BOARDS AND OTHER OBJECTS USING MULTIPLE SENSORS

CROSS-REFERENCE TO RELATED APPLICATION

This application claims the benefit of U.S. provisional application Ser. No. 62/115,849 filed Feb. 13, 2015, which is incorporated herein by reference.

FIELD

The present invention generally relates to an automated system and method for detecting defective edges of an object such as a printed circuit board, liquid crystal glass, plate, film or other substrate. In particular, the system and method can automatically detect defects, such as chips, cracks or bumps, on the object edges.

BACKGROUND

Objects, such as printed circuit boards (PCBs), liquid crystal glass, plates, films or other substrates that are generally substantially planar and rectangular in shape, occasionally develop defects such as chips, cracks or bumps along the object edges during fabrication or later. Some of these defects are minor and can be ignored because, for example, they are relatively small and will not affect the operation of the objects. However, larger defects that have the potential to adversely affect the proper operation or use of the object need to be identified so that appropriate action can be taken. For example, the object might be discarded. It may therefore be advisable to subject the edges of such objects to an automated inspection to check for defects.

One conventional automated system and method of detecting defects on the edge of an object uses a single electronic edge measurement sensor or position sensor. This arrangement is illustrated in FIG. 1A where an object such as a printed circuit board 1 is inspected by a single position sensor 10 that inspects the edge of board 1. Sensor 10 measures a value d1 that is the distance of the edge of the board detected by sensor 10 from a "0" point of the sensor, which is generally set to be at the center of the sensor. If there is a chip 5 along the board edge, it is determined whether d1 is less than $\varepsilon$, where $\varepsilon$ is a predetermined threshold value that is programmed by a user and corresponds to the maximum acceptable deviation of the board edge from the edge position that provides a "0" sensor reading. If $|d1| \le \varepsilon$, then a determination is made that the board is "normal." However, if $|d1| > \varepsilon$, then a determination is made that there is a defect. This manner of edge inspection may be adequate to detect a defective edge where the width of board 1 is fixed at a value W±$\varepsilon$ along the length of the board when there is no shifting/misalignment of the board in a sideways direction, tilting of the board, or fluctuation of board width (i.e., a change in width from one board to the next). If there is shifting, tilting or fluctuation, inspection with a single sensor is adequate where the amount of shifting, tilting, or fluctuation of board width is known and can be taken into account. However, even when a fluctuation $\lambda$ of the board width is taken into account, the edge detection performance will deteriorate because the threshold for generating a finding that a defect is present will increase from $\varepsilon$ to $\varepsilon+\lambda$ (i.e., $|d1| > \varepsilon+\lambda$).

FIG. 1B illustrates the consequence of allowing for a deviation of $\varepsilon$ in board width when inspecting board edges. The deviation of $\varepsilon$ is permitted to be in either direction, + or − from the "0" point of the sensor 10. Therefore, the deviation allows for the board width to possibly be as wide as W+$\varepsilon$ or as narrow as W−$\varepsilon$. Where the board width is W+$\varepsilon$, a chip 5 in the board edge can be as wide as 2$\varepsilon$ before the board will be determined to be defective.

FIG. 1C shows graphically the measured value that is detected by sensor 10 over time when there is a chip 5 in the left edge of board 1 and board 1 is moved in the direction shown by arrow 12 of FIG. 1A. As FIG. 1C shows, when board 1 is found to have one or more chips that exceed a threshold $\varepsilon$ (indicated by symbol 15), then board 1 is found to be defective.

FIGS. 1D and 1E illustrate the consequences of inspecting a board 11 that has no defective edges with a single sensor 10 where board 11 has been shifted to the right relative to sensor 10 by an amount $\Delta$. The shifting of board 11 relative to sensor 10 is indicated by the skewed arrow in FIG. 1D. As shown in FIG. 1E, the shifting can lead to a "false positive" edge detection measurement that exceeds a defect threshold $\varepsilon$ as indicated by symbol 15 even though there is no defect on the edges. As a result, a non-defective board will be rejected as defective, which is undesirable.

FIG. 2A shows another conventional manner of automated defect detection of object edges for defects such as chips, cracks or bumps using two aligned electronic sensors 10, 20, one for each of the opposite sides of an object such as printed circuit board 1 to be inspected. The distance between sensors 10, 20 is W. A movement of the left board edge to the left of sensor 10 or a movement of the right board edge to the right of sensor 20 (as shown) is measured as a negative movement, while a movement of a respective edge in the opposite direction is measured as a positive movement. FIG. 2A shows board 1 with a chip 5 along the left edge. The width of board 1 is approximately W±$\varepsilon$ along the length of the board and board 1 is shifted to the right from the center of sensors 10, 20 by a distance $\Delta$. A single combined measurement of both sensors 10, 20 is used to determine whether the board is chipped. As the board width W±$\varepsilon$ is fixed and the distance between the "0" point of the two sensors 10, 20 is set approximately equal to W, then status of the board can be judged as follows:

Normal: $|d1+d2| \le \varepsilon$
Defective: $|d1+d2| > \varepsilon$

Any shift value $\Delta$ is canceled out in calculating $|d1+d2|$. If the board width is as large as W+$\varepsilon$, a chip in the board edge can be as wide as 2$\varepsilon$, before it is detected as defective.

FIG. 2B shows a board 21 that has no defective edges but has a width that fluctuates by $\lambda$ from the width of another board to be inspected. This fluctuation can affect performance. If the fluctuation is known, it must be taken into account but the edge detection performance will deteriorate because the threshold for a chip to generating a finding that a defect is present will increase from $\varepsilon$ to $\varepsilon+\lambda$. If the fluctuation is not taken into account, then the fluctuation in width may be detected as a defect even though the board 21 is not defective.

FIG. 2C shows graphically the measured value of each of sensors 10, 20 over time when the board width fluctuates as shown in FIG. 2B. In FIG. 2C, sensor 10 is referred to as A and sensor 20 is referred to as B. FIG. 2D shows the result of adding A+B and comparing this sum to a threshold that is specified for the board. Where the width of board 21 fluctuates too greatly from the normal width, the board is improperly identified as defective by virtue of a "false positive" reading.

Thus, as noted above, one drawback of conventional defect detection techniques is that a possible shift of the board must be accounted for or a false positive defect detection may result. Moreover, a width fluctuation of a board can lead to a false positive finding of a nonexistent defect when only one or two sensors are used for edge inspection and the fluctuation is not specifically addressed. It would therefore be advantageous to have a more flexible system that accounts for possible board shifts/misalignments or fluctuations in the width of an object and provides correct indications of whether or not a board has defective edges.

SUMMARY

An automated system and method for detecting defective edges of an object such as a printed circuit board, liquid crystal glass, plate, film or other substrate is disclosed.

In embodiments, an automated system and method is provided for inspecting edges of objects, such as printed circuit boards, liquid crystal glass, plates, films or other substantially planar and rectangular substrates, that have substantially parallel, linear opposing edges for possible defects, such as chips, cracks or bumps. The system comprises a plurality of at least four electronic sensors that are able to detect object edges (such as electronic sensors that are used as position sensors or edge measurement sensors) in communication with a controller. As used in describing embodiments of the present invention, the terms "position sensors" or "edge measurement sensors" broadly refer to both sensors that may be limited in purpose to detecting positions or edges, respectively, and sensors that may also be used for other purposes as well such as for detecting object width. The electronic sensors are generally non-contact sensors, such as laser sensors or ultrasonic sensors, to name a few, so as to avoid contact with the objects that are scanned and to not damage the object or interfere with the sensor measurements. At least a first and second of the four electronic sensors are positioned on a first side of an object inspection line and at least a third and fourth of the four electronic sensors are positioned on a second side of the object inspection line substantially opposite the first and second electronic sensors, respectively. The first and third electronic sensors are substantially in alignment with each other and the second and fourth electronic sensors are substantially in alignment with each other. The controller is programmed to periodically, at specified measurement periods, obtain the substantially simultaneous sensor measurements of the first, second, third and fourth electronic sensors, to calculate a sum $E=|(A+B)-(C+D)|$ and to compare the sum E to a threshold value. The threshold value may be based on a tolerance value ε that is stored at the automated system or the threshold value may itself be stored at the automated system. The measurements of the first, second, third and fourth position sensors correspond to values A, C, B and D, respectively. In embodiments, the threshold value may be, for example, 2ε. In embodiments, the predetermined tolerance value ε may be a value that is object-specific and may be specified by a user. If the sum E is less than or equal to the threshold value, the controller continues to perform the algorithm until the board edges are scanned. However, in embodiments, if E is larger than the threshold value based on any set of sensor measurements, then the controller may trigger an action in response to a defect determination, such as activating an alarm, labeling a board as not passing inspection, or automatically diverting the board to a designated holding area for defective objects. In embodiments, such an action to be performed by the system may be triggered upon detection of a first chip or, in embodiments, the action may be deferred until the entire opposing edges of the board are inspected. The system may further comprise an input/output module to enter data, such as the predetermined tolerance value and other programming, and to obtain data such as a report of inspection results. The system may further comprise a display such as to display results, among other things.

In another embodiment, an automated system and method is provided for inspecting edges of objects, such as printed circuit boards, liquid crystal glass, plates, films or other substantially planar and rectangular substrates, that have substantially parallel, linear opposing edges for possible defects, such as chips, cracks or bumps. The system comprises a plurality of at least two electronic sensors (such as laser sensors or ultrasonic sensors, to name a few) in communication with a controller. A first of the two electronic sensors is positioned on a first side of the object inspection line and a second of the two electronic sensors is positioned substantially opposite the first electronic sensor on a second side of the object inspection line, wherein the first and second electronic sensors are substantially in alignment. The controller periodically, at specified measurement periods, obtains a first set of measurements A and B from the first and second electronic sensors substantially simultaneously at a first point in time, stores the first set of measurements, and periodically, at specified measurement periods, captures a second set of measurements C and D from the first and second electronic sensors thereafter substantially simultaneously at a second point in time. The controller is programmed to use the sensor measurements from the first and second electronic sensors at the first and second points in time to calculate a sum $E=|(A+B)-(C+D)|$ and to compare the sum E to a threshold value. The threshold value may be based on a tolerance value ε that is stored at the automated system or the threshold value may itself be stored at the automated system. In embodiments, the threshold value may be, for example, 2ε. In embodiments, the tolerance value ε is object-specific and may be specified by a user. In embodiments, if E is larger than the threshold value, then the controller is programmed to take an action in response to a defect determination to alert a user to the presence of a defect. However, if the sum E is less than or equal to the threshold value, no action is taken. The possible action that may be taken could be, for example, activating an alarm, labeling a board as not passing inspection, or automatically diverting the board to a designated place. The system may further comprise an input/output module to enter data, such as the object-edge-related value and other programming, and to obtain data such as a report of inspection results. The system may further comprise a display such as to display results, among other things.

In embodiments, the electronic sensors comprise laser sensors, which may include an emitter and a receiver to be mounted opposite one another such that the edge measurements are taken as an object edge intersects a light beam emanating from the emitter. In embodiments, the electronic sensors may be CMOS LED sensors.

BRIEF DESCRIPTION OF THE DRAWINGS

Exemplary embodiments of the present invention will be described with references to the accompanying figures, wherein:

FIG. 6 shows an isometric view of a portion of the conveyor of FIG. 4 illustrating the mounting of one of the electronic sensors, comprising an emitter and a receiver, along the conveyor in accordance with an exemplary embodiment of the present invention;

FIG. 8B is a graph of the values measured by the four electronic position sensors over time after scanning the edges of the object shown in FIG. 8A;

FIG. 8C is a graph of summed values of the measured values shown in FIG. 8B;

DETAILED DESCRIPTION

The present invention generally relates to a system and method for automated inspection of the substantially parallel edges of an object for a defect such as a chip, crack, or bump along either or both edges of opposite sides of the object. The object may be, for example, a printed circuit board, a liquid crystal glass, a plate, a film or other substantially planar substrate with edges that are designed to be substantially parallel and linear, but may not be substantially parallel in certain locations. This may be the result of manufacturing imperfections, or due to chips, cracks or bumps along the edges.

For discussion purposes, the description below generally refers primarily to a printed circuit board. However, a printed circuit board is just an example of an object that may be inspected by the system and method in accordance with exemplary embodiments of the present invention. While the discussion refers to the detection of defects on the edges along the "width" of the object, it should be understood that the edge detection according to embodiments of the present invention also encompasses detecting defects along lengthwise edges of an object.

Figure 3:
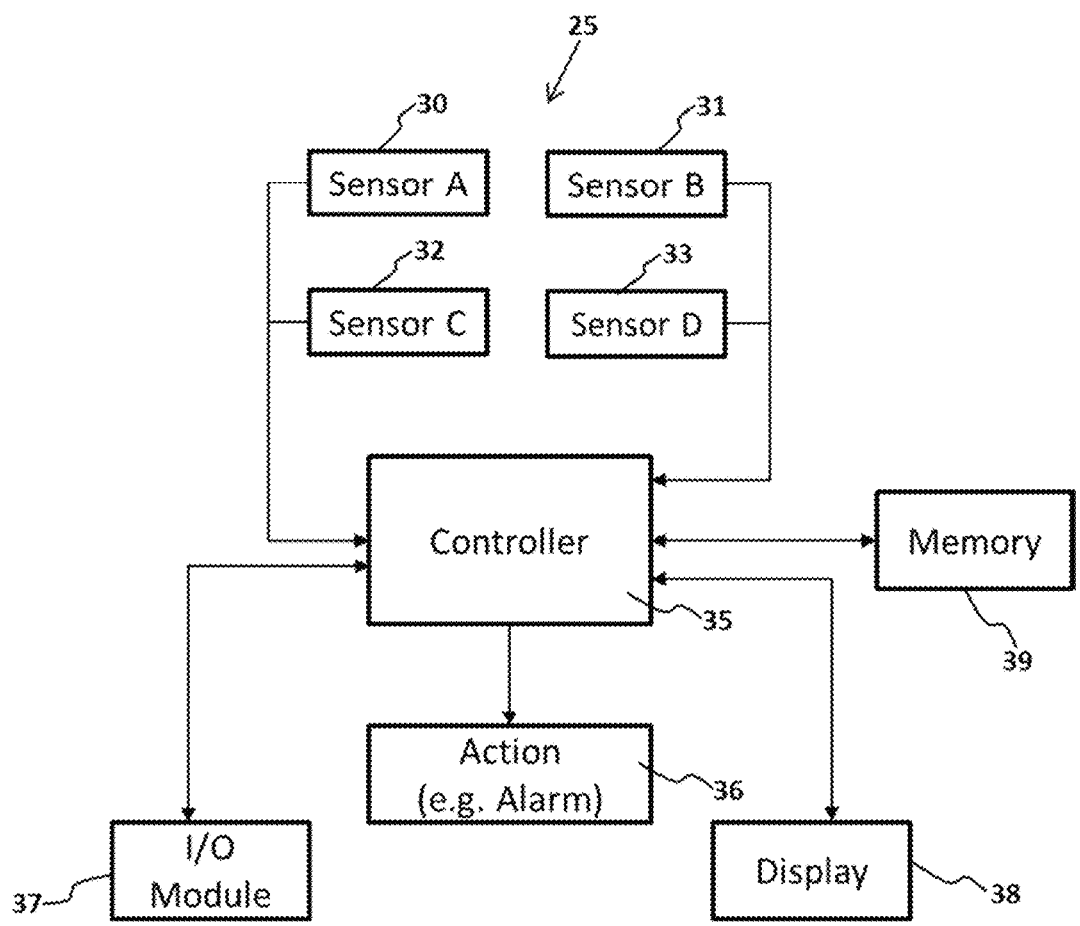
FIG. 3 is a block view of a system architecture for automatically detecting defective edges using a configuration of four electronic position sensors in accordance with an exemplary embodiment of the present invention.

FIG. 3 illustrates a system 25 that can be used to automatically detect edge defects in accordance with exemplary embodiments of the present invention. As shown in FIG. 3, the system 25 includes four electronic sensors 30, 31, 32, 33, configured as described below, for position/edge detection. System 25 also includes a multi-channel controller 35 that has at least four inputs to automatically obtain measurements from the four sensors 30-33. (In the embodiment of FIG. 12 described below, controller 35 need only have two inputs.) Controller 35 is programmed to use the obtained four substantially simultaneous sensor measurements from all four sensors to perform an algorithm for detecting defects, as described with reference to FIG. 7. System 25 may also include a notification mechanism 36, such as an alarm, to alert the operator regarding the detection of a significant defect that warrants action, by possibly flagging the board 1 as defective or diverting a defective board to a holding area. System 25 may further include an I/O module 37 for functions such as inputting parameters and any necessary programming and generating reports, a display 38 for displaying inspection respects or for other visual interaction with the system (such as when display 38 is a touch screen), and a memory 39 that stores tolerance value ε or a threshold value that is used for defect determinations. The system components may be linked with a wired connection and/or wirelessly.

Figure 4:
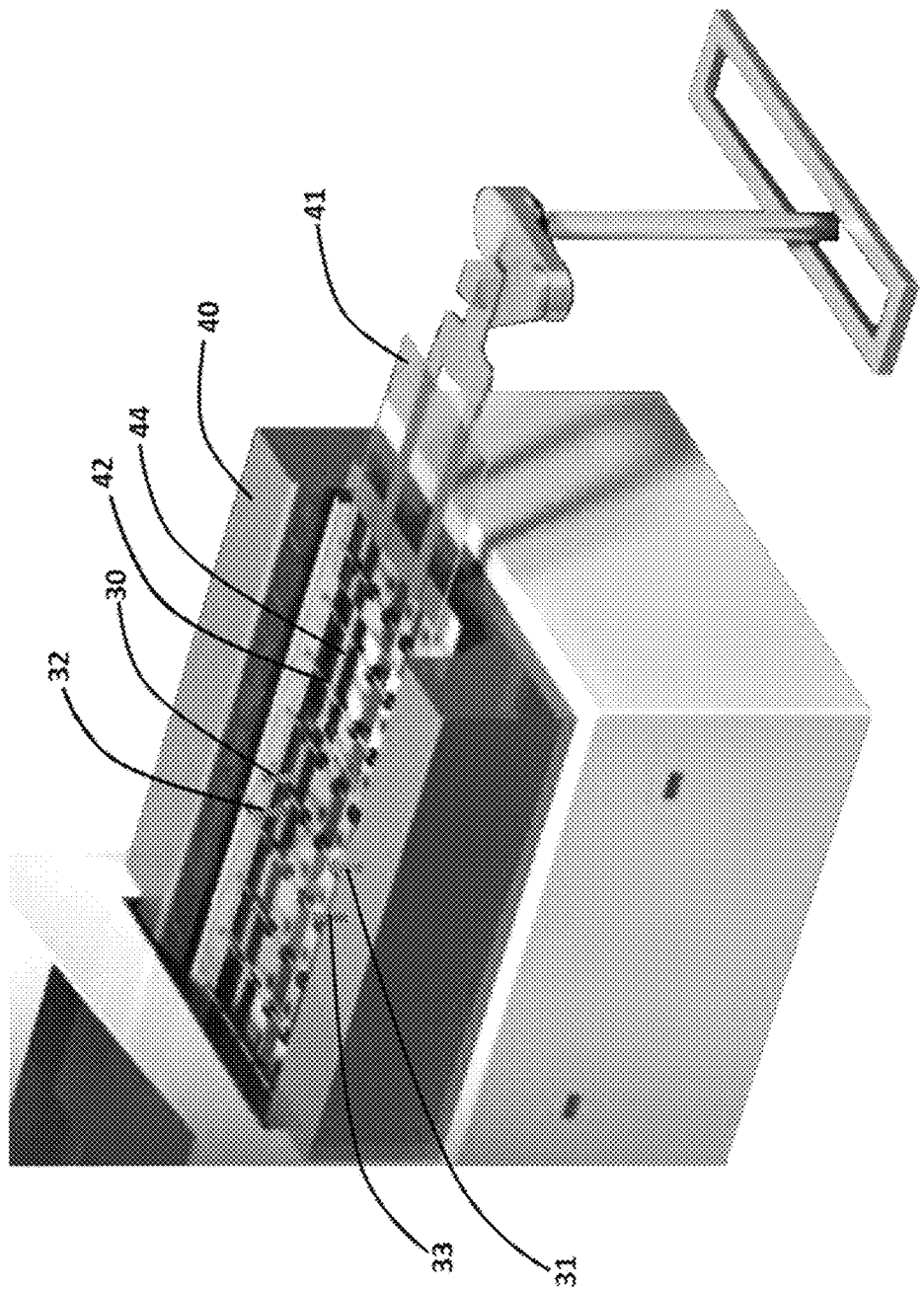
FIG. 4 is an isometric view of a portion of one example of a conveyor that can be used to transport the objects subject to edge defect detection relative to the four electronic position sensors in accordance with an exemplary embodiment of the present invention.

Referring to FIG. 4, in an exemplary embodiment of the present invention, system 25 operates, for example, in conjunction with a motorized conveyor 40 that serves as an inspection line on which objects are laid for inspection. However, the controls for system 25 can operate independently of the conveyor controls. Conveyor 40 moves the objects to be inspected through the electronic sensors 30-33 mounted to the sides of the conveyor 40 for detection of defective edges. Substrate 41 is shown in FIG. 4 as an example of one of the objects that is conveyed for inspection. The particular conveyor 40 that is used should generally be of a type that maintains the objects, to the extent possible, in a substantially horizontal position and substantially orthogonal to the sensors. The edges of the objects should be exposed to the sensors 30-33 that are mounted vertically above and/or below the objects. In embodiments, conveyor 40 may be comprised of a series of rotating metal rods 42 with pickup rollers 44, as shown in the example of FIG. 4. However, other types of conveyors may alternatively be used. The speed at which conveyor 40 moves can be substantially constant or may vary and is limited, at least in part, by the measurement period of sensors 30-33 that is required to take the measurements.

In another exemplary embodiment of the present invention, rather than use the conveyor of FIG. 4, it is possible to lay out the objects to be inspected in a stationary line for inspection and provide a motorized mechanism to move the sensors relative to the stationary boards. Or, in yet another exemplary embodiment, both the objects and sensors may move relative to one another in opposite directions. Thus, in FIG. 4, sensors 30-33 may be, in one embodiment, mounted to be stationary or, in another embodiment, mounted to be movable relative to the inspection line for sensor measurements.

Figure 5A:
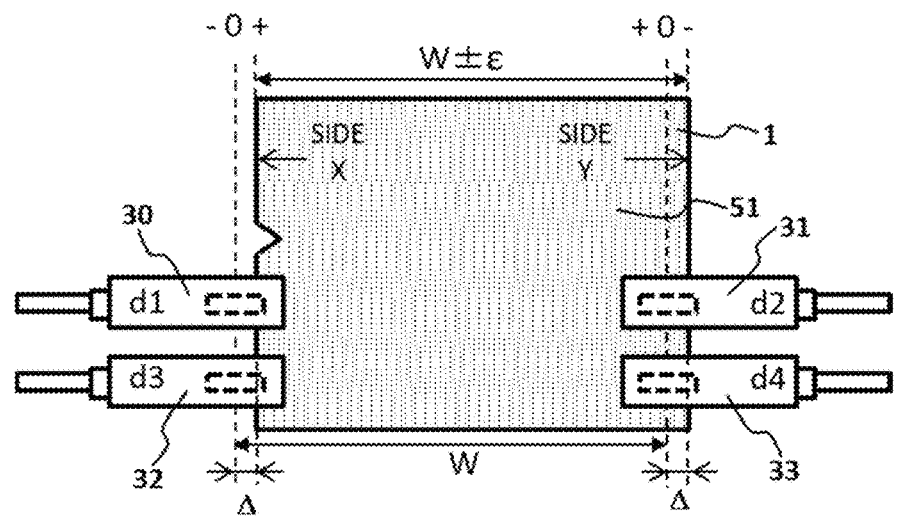
FIG. 5A is a top view of a substantially planar, rectangular object to be inspected for defective edges with the edge detection system that uses four electronic position sensors in accordance with an exemplary embodiment of the present invention.

Referring to FIG. 5A, electronic sensors 30-33 are positioned in a generally planar configuration with sensors 30, 32 positioned adjacent to and spaced apart from one another by an amount to detect the edges on one side X of a substantially rectangular object such as printed circuit board 51 and sensors 31, 33 are positioned along an opposite side Y of board 51 adjacent to and spaced apart from one another by approximately the same amount to detect the edges on opposite side Y of board 51. In one embodiment, the amount of spacing between sensors 30, 32 and between 31, 33 may be, for example, approximately 25 mm. However, the amount of spacing may alternatively be larger or smaller than 25 mm. Sensors 30, 32 are substantially linearly aligned and sensors 31, 33 are substantially linearly aligned in a direction substantially perpendicular to the direction of motion of board 51 relative to the sensors.

Figure 5B:
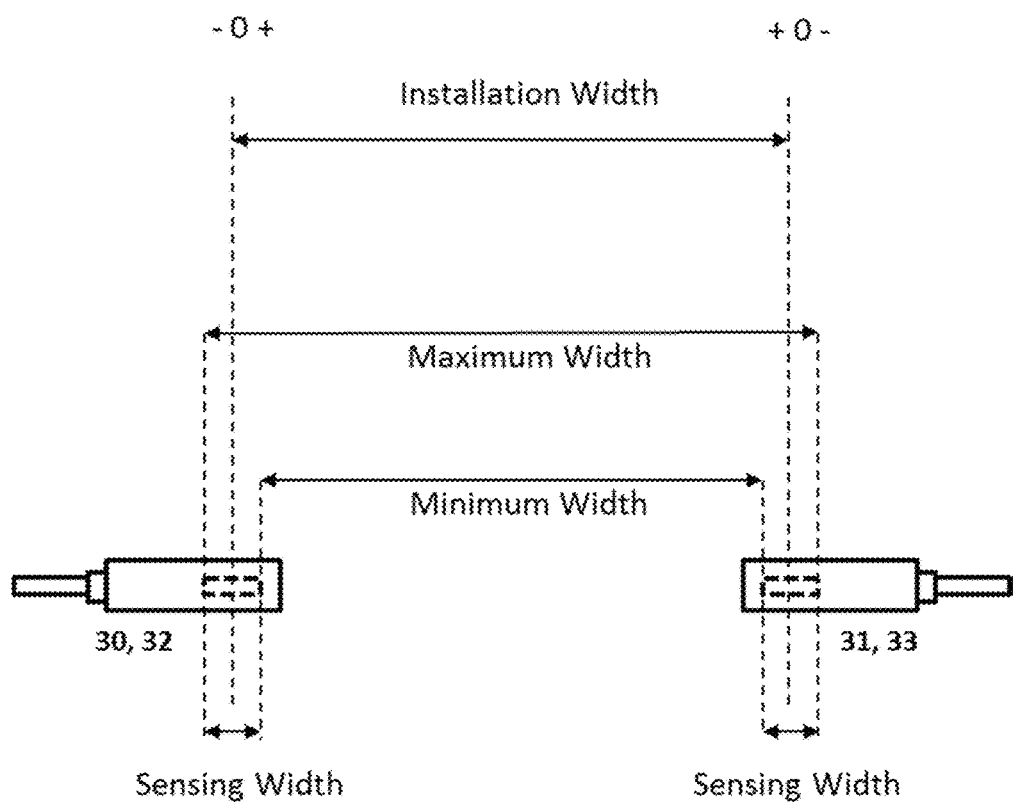
FIG. 5B is a plan view that illustrates the range of object widths whose edges can be inspected for defects given a particular installation width between electronic sensors located on opposite sides of the objects.

As shown in FIG. 5B, the spacing between sensors 30 and 31 and between sensors 32 and 33 on opposing sides should allow for a tolerance in the object width. Thus, the installation width, which is the width between the "0" points at approximately the center of sensors 30 and 32 and between the "0" points of sensors 31 and 33 should be selected appropriate to the width of the objects to be inspected. The sensor installation width on either side of the "0" points provides tolerances for movement of the object and/or for some variation in the width of the objects whose edges are inspected in accordance with an exemplary embodiment of the present invention.

FIG. 6 shows an isometric view of a portion of conveyor 40 with one of the four electronic sensors 30-33 in this figure depicted as a laser sensor that includes a sensor set of an emitter 30a and a receiver 30b with a generally flat light beam 34 of a specific width projected therebetween. Edge detection is performed when the edge of an object passes through light beam 34. While the use of a laser sensor is depicted as an example, any type of electronic sensor that can detect edges may be used.

In embodiments, one example of an electronic sensor that may be used with this system is a laser sensor, such as a CMOS LED sensor. A laser sensor includes both an emitter portion and a receiver portion. One such laser sensor is the K1G sensor from Azbil Corporation of Tokyo, Japan. Other examples of laser sensors include sensors from Keyence IG series (See http://www.keyence.com/products/sensor/positioning/ig/index.jsp) and Omron ZX-GT (laser CCD length measurement sensor—See http://www.fa.omron.co.jp/products/family/1918/).

As shown in FIG. 6, if laser sensors are used, one of the emitter and receiver portions of the sensor is positioned to be above the object to be inspected and the other portion is positioned below the object. An edge is detected with a laser sensor using Fresnel diffraction when the edge intersects the light emitted by the emitter portion of the sensor. Another example of a suitable electronic position sensor that may be used with the present invention is an edge measurement sensor, such as a sensor from the PBZ series, also available from Azbil Corporation of Tokyo, Japan. Although such precise specifications are not required by the present invention, it is noted, as a non-limiting example, that the K1G sensor has a resolution of approximately 0.1 µm, a measurement period of approximately 250 µs and a sensor measurement width of either approximately 7 mm or 15 mm.

An alternative type of electronic sensor that may be used for edge detection in accordance with other embodiments of the present invention is an ultrasonic sensor. An example of a suitable ultrasonic sensor is an Edge Detection Ultrasonic Sensor, Model US-U30AN from TAKEX, Takenaka Electronic Industrial Co., Ltd. of Kyoto, Japan.

In general, the electronic sensors that are used should not make contact with the object being inspected. This is particularly significant when inspecting the edges of vulnerable objects, such as those that can break when pressed on, such as glass substrates and thin films. Additionally, non-contact sensors should generally be used where the accuracy of the sensor measurements may be negatively impacted, such as may occur when measuring a wet object.

Figure 7:
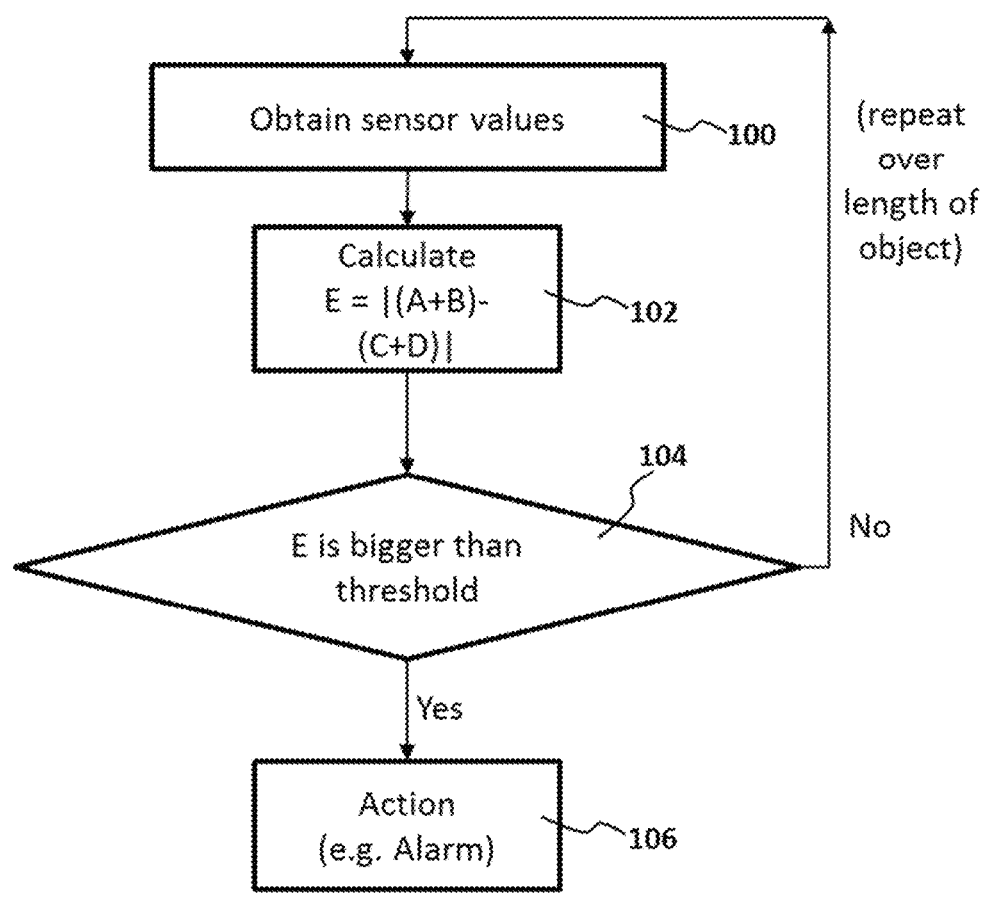
FIG. 7 is a flow chart that illustrates an edge defect detection algorithm performed by the controller in accordance with an exemplary embodiment of the present invention.

Controller 35 is programmed to obtain periodic readings of electronic sensors 30-33 and to perform the algorithm of FIG. 7 that determines whether a defect is detected at the edge of the printed circuit board. The periodicity of the readings is generally limited by the measurement period of the electronic sensors (e.g., 250 µs). In embodiments, one example of a controller that may be used is a K1G Series controller from Azbil Corporation.

FIG. 7 is a flow chart that illustrates an edge defect detection algorithm performed by controller 35. At step 100, the values that are simultaneously generated by sensors 30-33 are obtained by controller 35. At step 102, controller 35 calculates the value $E=|(A+B)-(C+D)|$, where A is the value generated by sensor 30, B is the value generated by sensor 31, C is the value generated by sensor 32 and D is the value generated by sensor 33. The values A, B, C, and D represent respective distances d1, d2, d3, and d4 that are measured by the sensors between the detected edge of the board being inspected and the "0" point of the respective sensor, which is generally situated approximately at the center of the sensor. A movement of the left board edge to the left of sensors A or C or a movement of the right board edge to the right of sensor B or D (as shown) is measured as a negative movement, while a movement of a respective edge in the opposite direction is measured as a positive movement. Because these four sensor values are obtained, it is not necessary to also obtain the board width targeted by the board design specifications for an edge defect determination.

At step 104, it is determined whether the value of the E is larger than a threshold value that is based upon an input into system of a value ε. The specified tolerance value ε should account for the board layout, including the proximity of the components on the board to the board edge, and should account for possible roughness of the board edges that may cause the board edges to not be precisely parallel. As a non-limiting example, the tolerance value ε may be approximately 1 mm or it may be larger or smaller than that. As an example, the threshold value may be 2ε, which 2×ε. As an alternative to comparing the value of E to a threshold value based upon the value ε, the threshold value may itself be stored and compared to the value of E. If E is greater than the threshold, an action is triggered at step 106 to indicate a defect, such as a chip, crack or bump. If no defect, such as a chip, crack or bump, is detected, the measurement of sensor values continues as the board moves relative to the electronic sensors in a process that continues through the length of the board (except at the extreme ends of the board where the board intersects only two opposing electronic sensors). The algorithm is repeated for each board that is to be inspected.

Referring to FIG. 5A, in this example, the board 1 moves relative to the respective positions of the sensors 30-33. Board 1 may be shifted to the right by a so-called "misalignment value" Δ, which measures the misalignment of the board compared to the "0" value position of each sensor when measuring a non-chipped edge. Using the algorithm of FIG. 7 where value E=|(A+B)−(C+D)| where the values A through D correspond to distances d1, d2, d3 and d4 as measured by the sensors 30, 31, 32, 33 respectively, the equations for judging whether a board of width W is acceptable or is defective are as follows:

Normal: |d1+d2−d3−d4|≤2ε

Defective: |d1+d2−d3−d4|>2ε          Equation (1)

As noted above, in one embodiment, ε corresponds to a tolerance value that specifies the board width deviation that is permitted and 2ε corresponds to the threshold value for detecting a defect. In another embodiment, the threshold value 2ε may itself be stored instead of storing the tolerance value. If there were no misalignment and no defect, d1=d3 and d2=d4, and a determination is therefore made that the inspected edges of the board are not defective. However, if there is a misalignment, the misalignment is accounted for because any movement of the board to the right, for example, which is detected by electronic sensors 30, 32 is accounted for and subtracted out by the measurements at electronic sensors 31, 33.

Figure 8A:
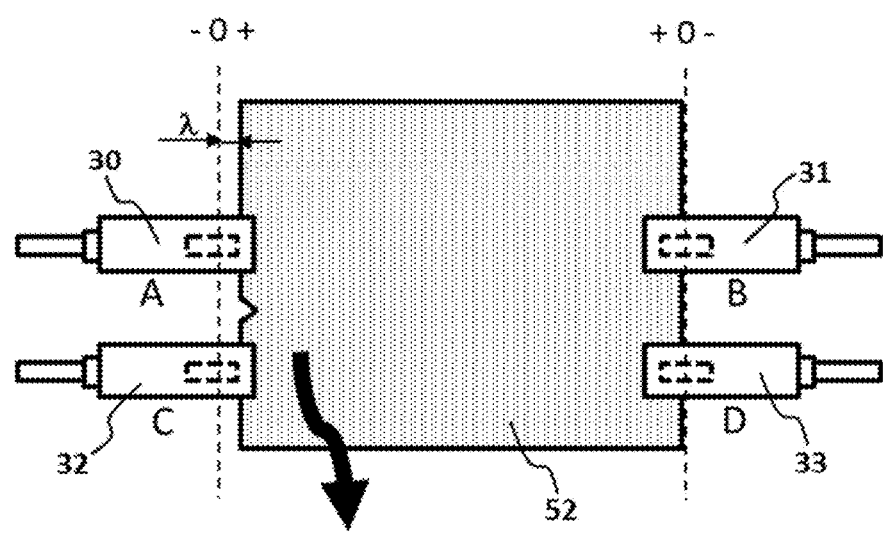
FIG. 8A is a top view of an object that has a width that is narrower than normal by λ being inspected for defects along its edges in accordance with an exemplary embodiment of the present invention.

FIG. 8A illustrates a scenario where a board 52 with a chip along the left edge is less than a normal width W so that the left edge of board 52 is located to the right of electronic sensors 30, 32 by a distance λ. In this case, the measured values of electronic sensors 30, 32 (respectively A, C in the figure) over time shown in FIG. 8B will detect the chip, with the detection by electronic sensor 30 preceding the detection by electronic sensor 32. While the chip on board 52 will be detected, there will not be a false positive due to the less than normal board width because the calculations in equation (1) will take into account and cancel out the fluctuation λ from the normal width at both electronic sensors 30, 32. FIG. 8C shows graphically the sum of the measured values of FIG. 8B.

As noted above, because of the configuration of the four electronic sensors and the algorithm used as in an exemplary embodiment of the present invention, it is unnecessary to provide the system 25 with a predetermined width W of the printed circuit board. As a result, boards of somewhat differing width may be inspected by the system without changing the locations of the electronic sensors. Moreover, a fluctuation λ of board width will not affect performance of the edge detection system and method. Thus, there will not be a false reading that there is a defect when the widths of the boards to be inspected fluctuate from board to board and a non-defective board simply has a width that is different from the width of another board on the inspection line.

Figure 9:
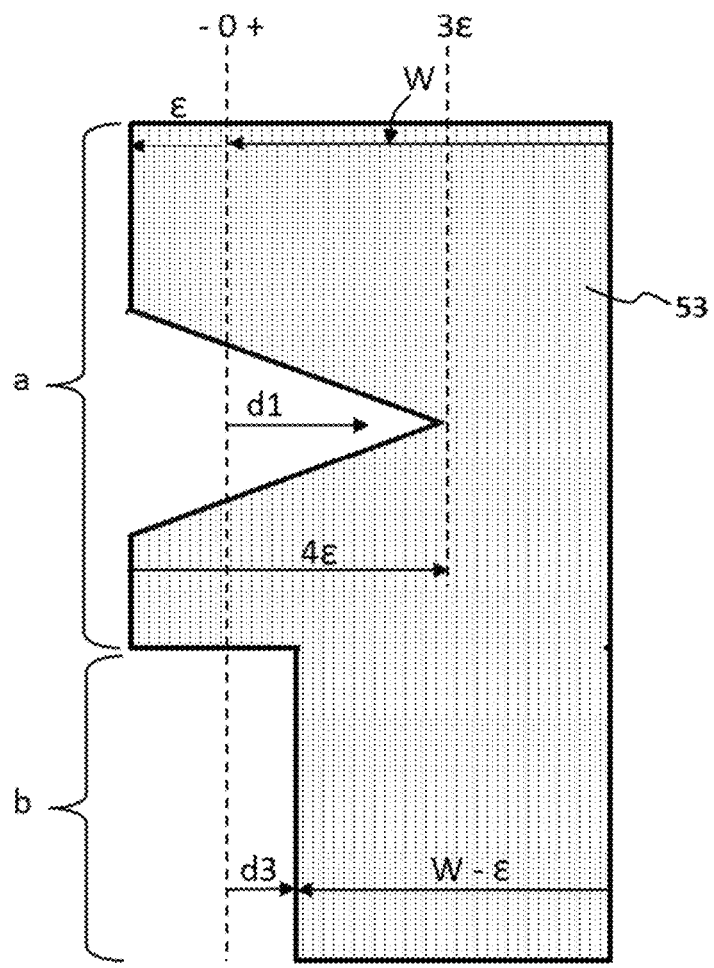
FIG. 9 shows an enlarged view of an edge along a portion of a board that illustrates a maximum chip size that is allowed using the edge defect detection method in accordance with an exemplary embodiment of the present invention.

Referring to FIG. 9, a portion of the chipped left edge of board 53 is shown. For illustrative purposes only, board 53 is shown with segments "a" and "b" that differ in width. The width of segment "a" is W+ε while the width of board 53 in segment "b" is d3=W−ε. Because equation (1) has a threshold value of 2ε, the maximum width of a chip, crack or bump on the edge of a board 53 without a finding of a defective edge will be 4ε, as illustrated.

Figure 10A:
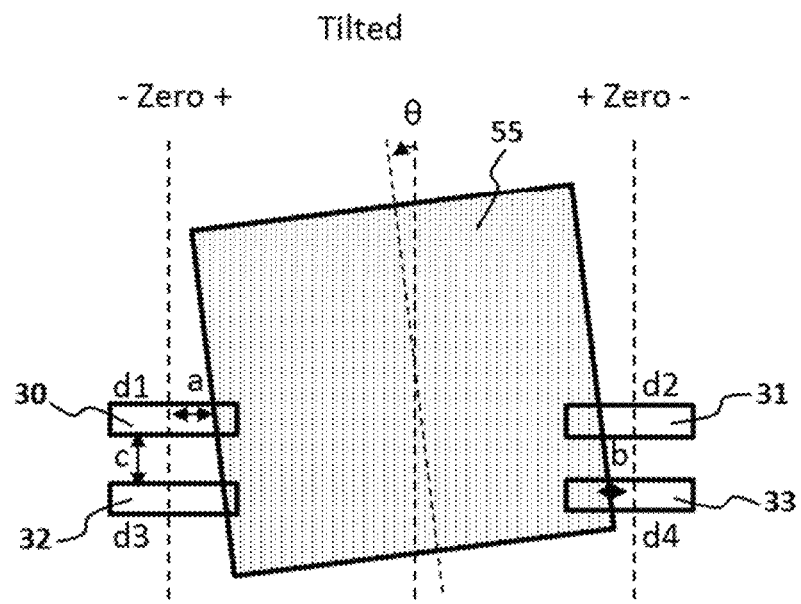
FIG. 10A is a top view of an object that is inspected by four electronic sensors while tilted from an orthogonal position in accordance with an exemplary embodiment of the present invention.
Figure 10B:
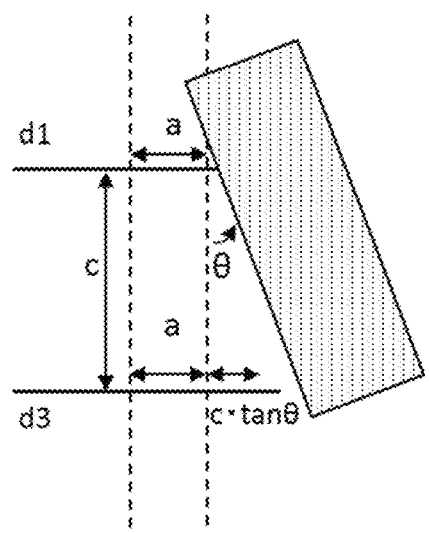
FIG. 10B is another view of a tilted object as shown in FIG. 10A in accordance with an exemplary embodiment of the present invention.

FIGS. 10A and 10B provides an example that demonstrates that the use of four electronic sensors in the configuration of FIG. 5A along with the algorithm in accordance with an exemplary embodiment of the present invention negates the impact of a misalignment or tilt in circuit board 55 by an angle θ as it is passes through the electronic sensors. In this instance, d1=a, d3=a+c·tan θ, d2=b+c·tan θ, and d4=b. Therefore, d1+d2−d3−d4=a+b+c·tan θ−a−b−c·tan θ=0.

As a result of the present invention, boards with widths that are within the sensing width of the electronic sensors and that have a common tolerance value ε, can be inspected one after the other without stopping to reprogram the system for each exact board width W. Moreover, misalignment or tilting of the boards during edge inspection is addressed.

Figure 1A:
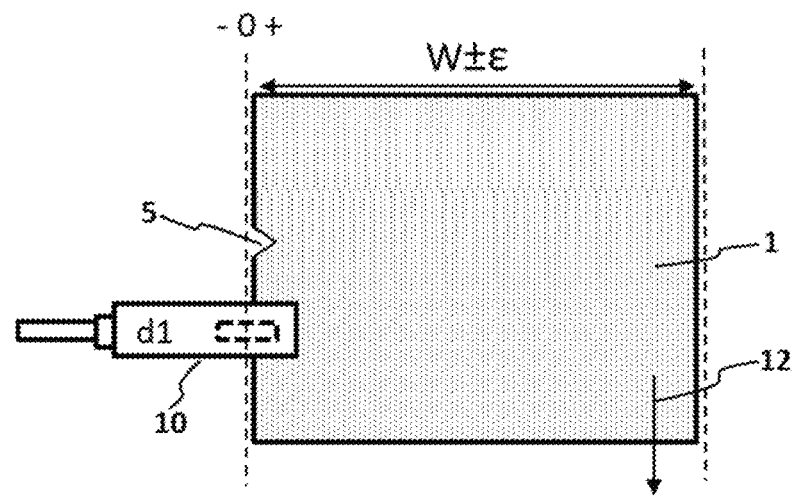
FIG. 1A is a top view of a substantially planar, rectangular object to be inspected for defective edges with a conventional edge detection system that uses a single electronic position sensor.
Figure 1B:
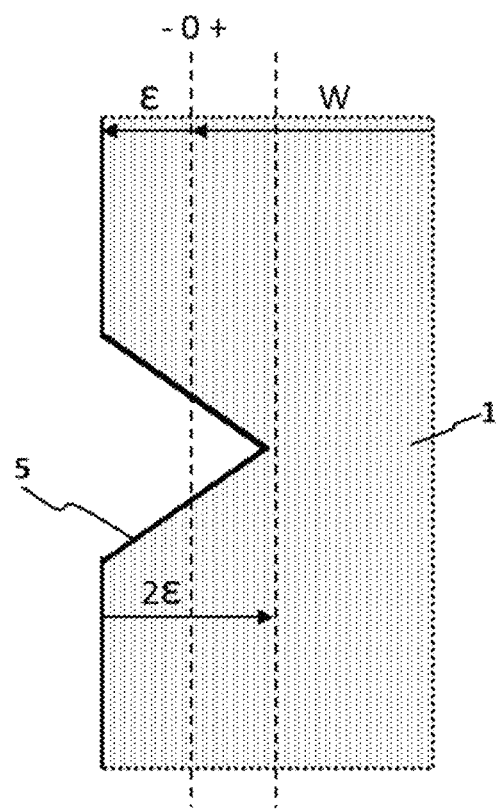
FIG. 1B is a top view of an enlarged section of the object of FIG. 1A showing a chip on the left edge of the object.
Figure 1C:
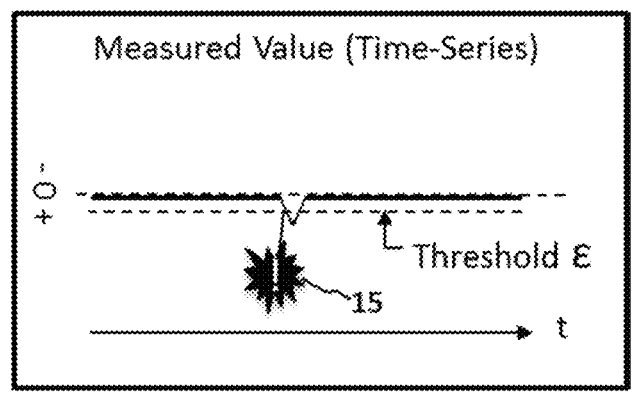
FIG. 1C is a graph of the values measured by the single position sensor over time after scanning the left edge of the object as shown in FIG. 1A.
Figure 1D:
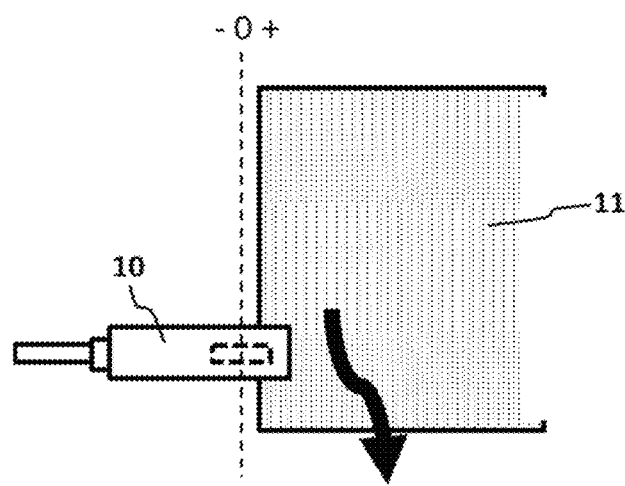
FIG. 1D is a top view of an object with non-defective edges being scanned where the object is shifted to the right relative to the position sensor beam.
Figure 1E:
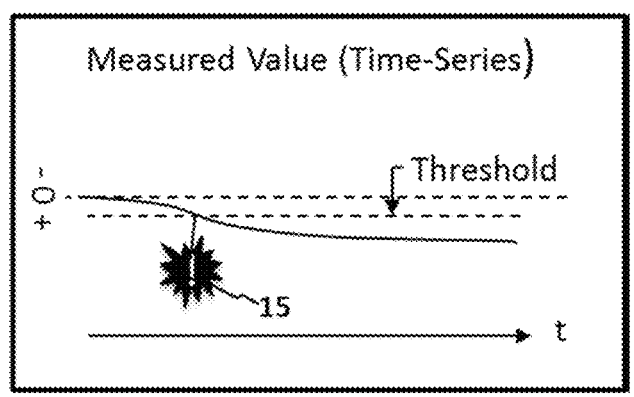
FIG. 1E is a graph of the values measured by the single position sensor over time after scanning the edge of the shifted object shown in FIG. 1D.
Figure 2A:
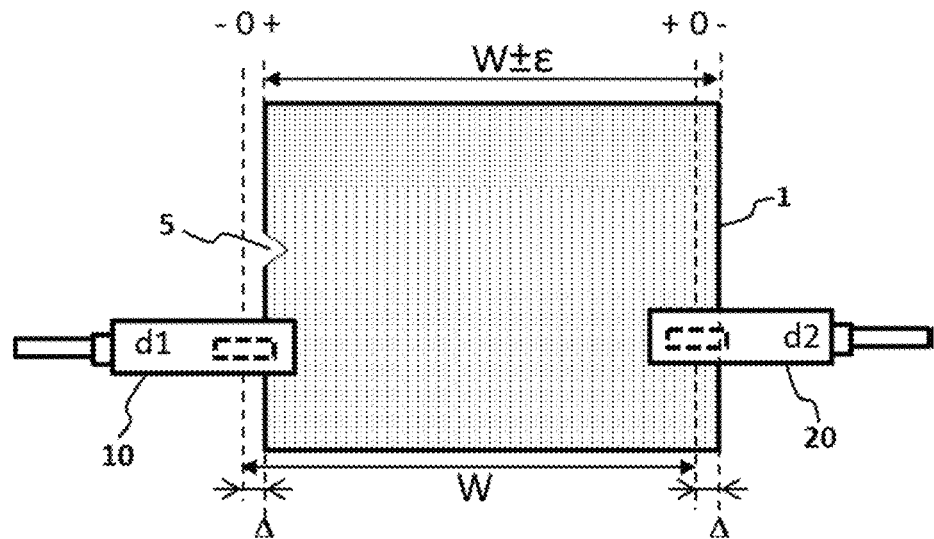
FIG. 2A is a top view of an object of normal width to be inspected for defective edges with a conventional edge detection system that uses two position sensors.
Figure 2B:
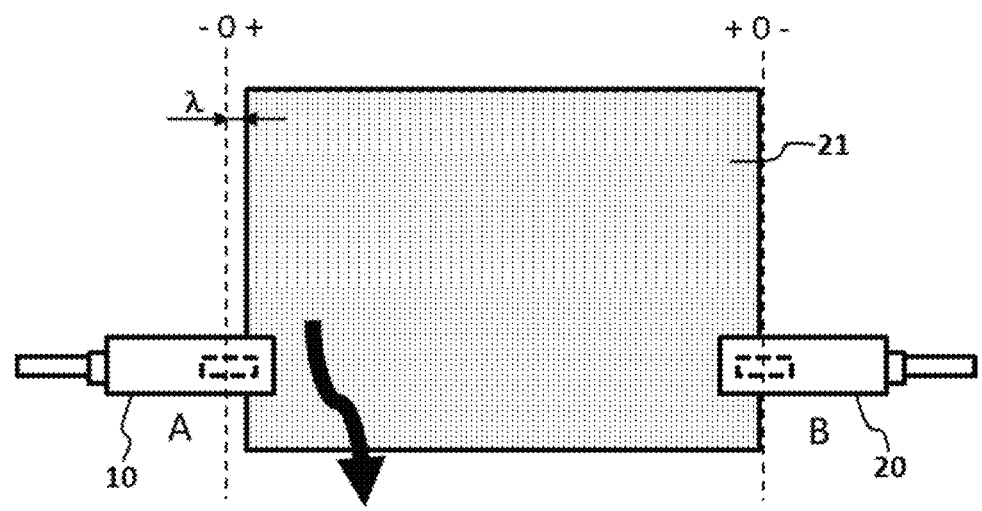
FIG. 2B is a top view of an object of less than normal width being scanned by the position sensor beam.
Figure 2C:
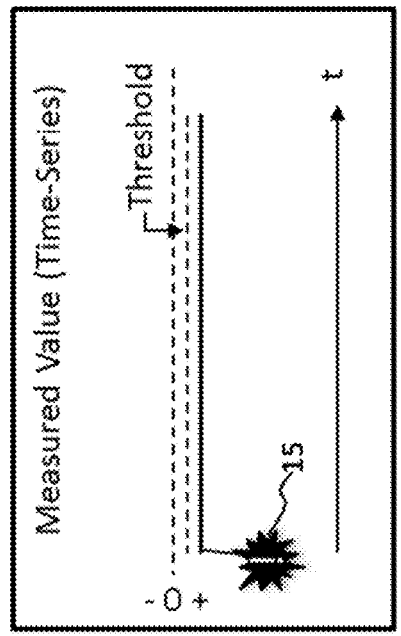
FIG. 2C is a graph of the values measured by the two position sensors over time after scanning the opposing edges of the object shown in FIG. 2B.
Figure 2D:
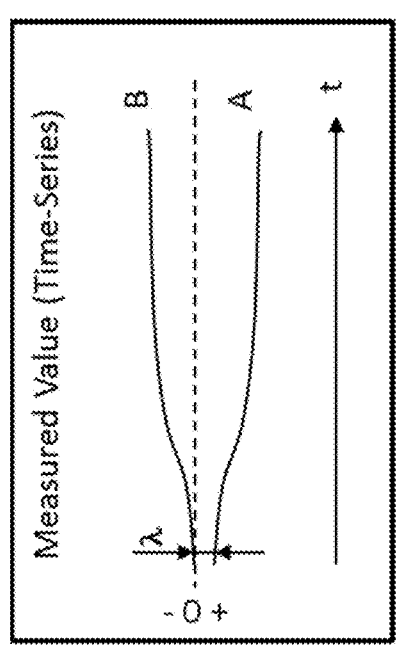
FIG. 2D is a graph of the sum of the values measured by two position sensors over time after scanning the opposing edges of the object shown in FIG. 2B.

It is recognized that the minimum detectable defect is double in size, i.e., 2ε, compared to the prior art system and method that uses just two electronic sensors, as described with reference to FIG. 2A, because of the calculations that are performed. However, where ε is a relatively small value compared to the size of the defect such as a chip that needs to be detected, the difference between ε and 2ε is not particularly significant.

Figure 11:
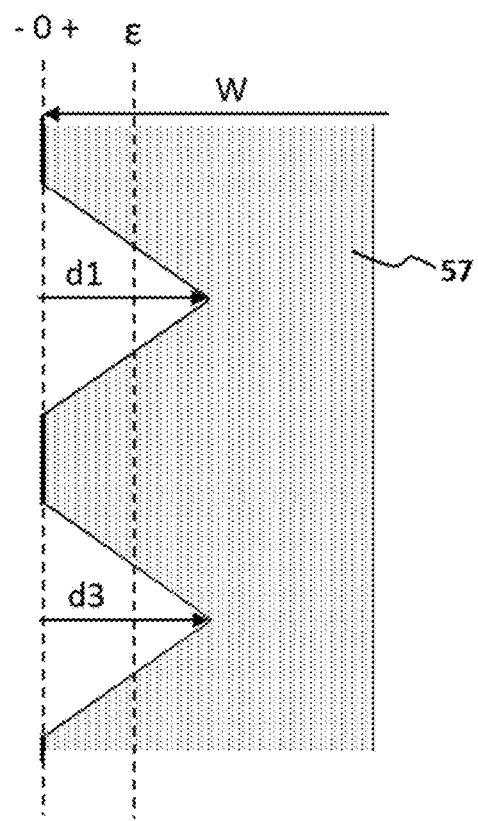
FIG. 11 is an enlarged view of a portion of an object edge that has two chips of identical size and shape.

FIG. 11 illustrates a situation where two almost identically sized chips on one side of the printed circuit board 57 are spaced apart by the same distance as the distance between the electronic sensors on that side (e.g., the distance between electronic sensors 30 and 32). In this case, when electronic sensors 30 and 32 are both taking measurements of the identical chips, performing the calculation E=|(A+B)−(C+D)| will cause the effects of both chips on the board to cancel each other out such that the board 57 will not be identified as defective at that moment. This is not a concern because the board will still be identified as defective at an earlier or later point during the inspection of the board edge when only one of the electronic sensors 30, 32 on the left side detects a chip while the other electronic sensor is measuring an unchipped part of the edge.

Figure 12:
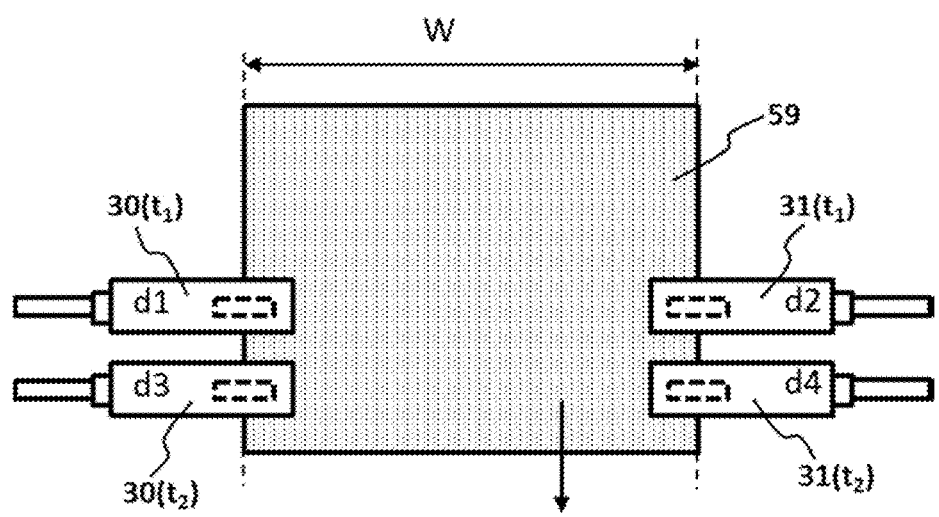
FIG. 12 is a top view of an object that is inspected by two electronic sensors where the two readings of the two electronic sensors are used by a controller to perform the algorithm of FIG. 7 in accordance with another exemplary embodiment of the present invention.

In another exemplary embodiment of the system and method of the present invention, board edges of a board 59 are detected with only two electronic sensors 30, 31 as shown in FIG. 12, but the measurements are obtained from the same two electronic sensors at two different times $t_1$ and $t_2$ (which is later in time than time $t_1$) spaced apart from one another by an appropriate time interval (e.g. 1 sec) that is dependent on conveyor speed and the desired level of accuracy. The algorithm of FIG. 7 is performed with the first set of measured values 30($t_1$), 31($t_1$) for electronic sensors 30, 31 at $t_1$ inserted into equation (1) as values A and B and the second set of measured values 30($t_2$), 31($t_2$) for electronic sensors 30, 31 at $t_2$ inserted into equation (1) as values C and D (at step 102). The resulting value E is compared to a threshold 2ε to determine whether defects are present (at step 104). Values 30($t_1$), 31($t_1$) are stored in memory 39 until retrieved at step 100 for use with values 30($t_2$), 31($t_2$) in equation (1) (step 102).

While particular embodiments of the present invention have been shown and described in detail, it would be obvious to those skilled in the art that various modifications and improvements thereon may be made without departing from the spirit and scope of the invention. It is therefore intended to cover in the appended claims all such modifications and improvements that are within the scope of this invention.

We claim:
1. An automated system for inspecting edges of one or more objects for possible defects, the system comprising:
at least a first set of four electronic sensors to detect positions of opposing edges of one or more objects, wherein a first electronic sensor and a second electronic sensor of the first set of four electronic sensors are positioned on a first side of an inspection line along which the one or more objects are placed to inspect a first object edge for defects and a third electronic sensor and a fourth electronic sensor of the first set of four electronic sensors are positioned on a second side of the inspection line substantially opposite the first and second electronic sensors, respectively, to inspect a second object edge on an opposite side of the first object edge for defects, wherein the first and third electronic sensors are maintained in substantial alignment with each other and the second and fourth electronic sensors are maintained in substantial alignment with each other; and
a controller programmed to periodically obtain a set of substantially simultaneous measurements from the first, second, third and fourth electronic sensors as the first and second object edges of a respective object are scanned by the first set of four electronic sensors, to calculate a sum $E=|(A+B)-(C+D)|$, and to compare the sum E to a threshold value, where A, C, B and D correspond to the set of substantially simultaneous measurements obtained from the first, second, third and fourth electronic sensors, respectively;
wherein, when the sum E remains less than or equal to the threshold value, the controller is programmed to continue to periodically obtain additional sets of substantially simultaneous measurements from the first, second, third and fourth electronic sensors until the scanning of the first and second object edges of the respective object is completed but, if the sum E exceeds the threshold value during scanning of the first and second object edges of the respective object, the controller determines that the respective object has a defective edge,
wherein A represents a first distance between a first reference point on the first electronic sensor and a first position on the first object edge;
wherein C represents a second distance between a second reference point on the second electronic sensor and a second position on the first object edge;
wherein B represents a third distance between a third reference point on the third electronic sensor and a first position on the second object edge; and
wherein D represents a fourth distance between a fourth reference point on the fourth electronic sensor and a second position on the second object edge.

2. The system of claim 1, wherein the controller is further programmed to cause an object having a defective edge to be removed from the inspection line.

3. The system of claim 1, wherein one or more of the first set of four electronic sensors are laser sensors.

4. The system of claim 1, wherein the threshold value to which the sum E is compared is based on a tolerance value that is allowed for an object width of the one or more objects.

5. The system of claim 4, further comprising a memory to store at least one of the threshold value and the tolerance value.

6. A method for automatically inspecting edges of one or more objects for possible defects, the method comprising:
scanning opposing, first and second object edges of one or more objects using at least a first set of four electronic sensors, wherein a first electronic sensor and a second electronic sensor of the first set of four electronic sensors are positioned on a first side of an inspection line along which the one or more objects are placed to inspect the first object edge for defects and a third electronic sensor and a fourth electronic sensor of the first set of four electronic sensors are positioned on a second side of the inspection line substantially opposite the first and second electronic sensors, respectively, to inspect the second object edge on an opposite side of the first object edge for defects; wherein the first and third electronic sensors are maintained in substantial alignment with each other and the second and fourth electronic sensors are maintained in substantial alignment with each other, and wherein the opposing first and second object edges of the one or more objects are scanned for inspection by the first set of four electronic sensors as the first and second object edges pass in proximity to the first set of four electronic sensors;
periodically obtaining, by a controller, a set of substantially simultaneous measurements from at least the first set of four electronic sensors for a first object of the one or more objects as the first and second objects edges of the first object are scanned by the electronic sensors; and
for each periodically obtained set of substantially simultaneous measurements,
(i) summing, by the controller, the periodically obtained set of substantially simultaneous measurements from the first, second, third and fourth electronic sensors, to calculate a sum $E=|(A+B)-(C+D)|$, where A, C, B and D correspond to substantially simultaneous measurements obtained from the first, second, third and fourth electronic sensors, respectively; and
(ii) comparing, by the controller, the sum E to a threshold value;
wherein, when the sum E remains less than or equal to the threshold value, the controller continues to periodically obtain additional sets of substantially simultaneous measurements from the first, second, third and fourth electronic sensors until the scanning of the first and second object edges of the first object is completed, and wherein, if the sum E exceeds the threshold value during the scanning of the first and second object edges of the first object, the controller determines that the first object has a defective edge;

wherein A represents a first distance between a first reference point on the first electronic sensor and a first position on the first object edge;

wherein C represents a second distance between a second reference point on the second electronic sensor and a second position on the first object edge;

wherein B represents a third distance between a third reference point on the third electronic sensor and a first position on the second object edge; and wherein D represents a fourth distance between a fourth reference point on the fourth electronic sensor and a second position on the second object edge.

7. The method of claim 6, further comprising removing the object from the inspection line when the object is determined to have the defective edge.

8. The method of claim 6, wherein one or more of the at least four electronic sensors are laser sensors.

9. The method of claim 6, wherein the threshold value to which the sum E is compared is based on a tolerance value that is allowed for an object width of the one or more objects.

10. The method of claim 9, further comprising storing at least one of the threshold value and the tolerance value.

11. The system of claim 1, wherein each of the first, second, third and fourth reference points represent a respective center point of the respective first, second, third and fourth electronic sensors.

12. The system of claim 1, wherein one or more electronic sensors of the first set of four electronic sensors have a substantially flat light beam.

13. The method of claim 6, wherein each of the first, second, third and fourth reference points represent a respective center point of the respective first, second, third and fourth electronic sensors.

14. The method of claim 6, wherein one or more electronic sensors of the first set of four electronic sensors have a substantially flat light beam.

* * * * *